United States Patent
Kaneda et al.

(10) Patent No.: US 10,117,857 B2
(45) Date of Patent: Nov. 6, 2018

(54) EXTERNAL MEDICINE FOR DIFFUSE PLEXIFORM NEUROFIBROMA

(71) Applicant: OSAKA UNIVERSITY, Osaka (JP)

(72) Inventors: Mari Kaneda, Osaka (JP); Ichiro Katayama, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 15/559,322

(22) PCT Filed: Mar. 9, 2016

(86) PCT No.: PCT/JP2016/057330
§ 371 (c)(1),
(2) Date: Sep. 18, 2017

(87) PCT Pub. No.: WO2016/152519
PCT Pub. Date: Sep. 29, 2016

(65) Prior Publication Data
US 2018/0110759 A1    Apr. 26, 2018

(30) Foreign Application Priority Data

Mar. 23, 2015 (JP) ................................. 2015-059041

(51) Int. Cl.
| | | |
|---|---|---|
| A61K 31/436 | (2006.01) |
| A61K 47/10 | (2017.01) |
| A61K 9/06 | (2006.01) |
| A61P 35/00 | (2006.01) |

(52) U.S. Cl.
CPC .............. *A61K 31/436* (2013.01); *A61K 9/06* (2013.01); *A61K 47/10* (2013.01); *A61P 35/00* (2018.01)

(58) Field of Classification Search
CPC .................................................. A61K 31/436
USPC ....................................................... 514/326
See application file for complete search history.

(56) References Cited

U.S. PATENT DOCUMENTS

| | | | |
|---|---|---|---|
| 2010/0305150 A1 | 12/2010 | Berg et al. |
| 2013/0317053 A1 | 11/2013 | Kaneda et al. |

FOREIGN PATENT DOCUMENTS

| | | |
|---|---|---|
| JP | 2009-525294 | 7/2009 |
| WO | 2006/071966 | 7/2006 |
| WO | 2012/105521 | 8/2012 |

OTHER PUBLICATIONS

Washington et al., Hawaii Med. J. (2010), vol. 69, pp. 191-193.*
Ito, Toshihiro "Origin of Melanin Containing Cells of Diffuse Plexiform Neurofibroma in Patients with Neurofibromatosis 1", Jikeikai Medical Journal, 2002, vol. 117, No. 4, pp. 277 to 284, abstract, I . English abstract provided.
Sato, Chiemi et al., "Suppressive effects of rapamycin and lovastatin on primarily isolated fibroblasts and Schwann cells from neurofibromas in vitro", nichire-byokaishi, 2014, pp. 55 to 58, English abstract provided.
Yuichi Yoshida et al., "Diagnosis and Treatment of Neurofibromatosis Type 1 (NF1)", Japanese Journal of Dermatology, 2012, vol. 122, No. 13, pp. 3189 to 3191, Hajimeni, 2., 4., fig. 1, table 1.
International Search Report for PCT/JP2016/057330, dated Jun. 7, 2016.
English Translation of International Preliminary Report on Patentability for PCT/JP2016/057330, dated Oct. 5, 2017.
Weiss, Brian et. al., "Sirolimus for Non-Progressive NF1-Associated Plexiform Neurofibromas: An NF Clinical Trials Consortium Phase II Study" Pediatr Blood Cancer 2014, 61, 982-986.

* cited by examiner

*Primary Examiner* — Taofiq A Solola
(74) *Attorney, Agent, or Firm* — Casimir Jones, SC; Robert A. Goetz

(57) ABSTRACT

An external medicine for diffuse plexiform neurofibromas is provided. The external medicine for diffuse plexiform neurofibromas in accordance with an embodiment of the present invention contains, as an active ingredient, at least one selected from the group consisting of sirolimus and sirolimus derivatives.

Figure 1:
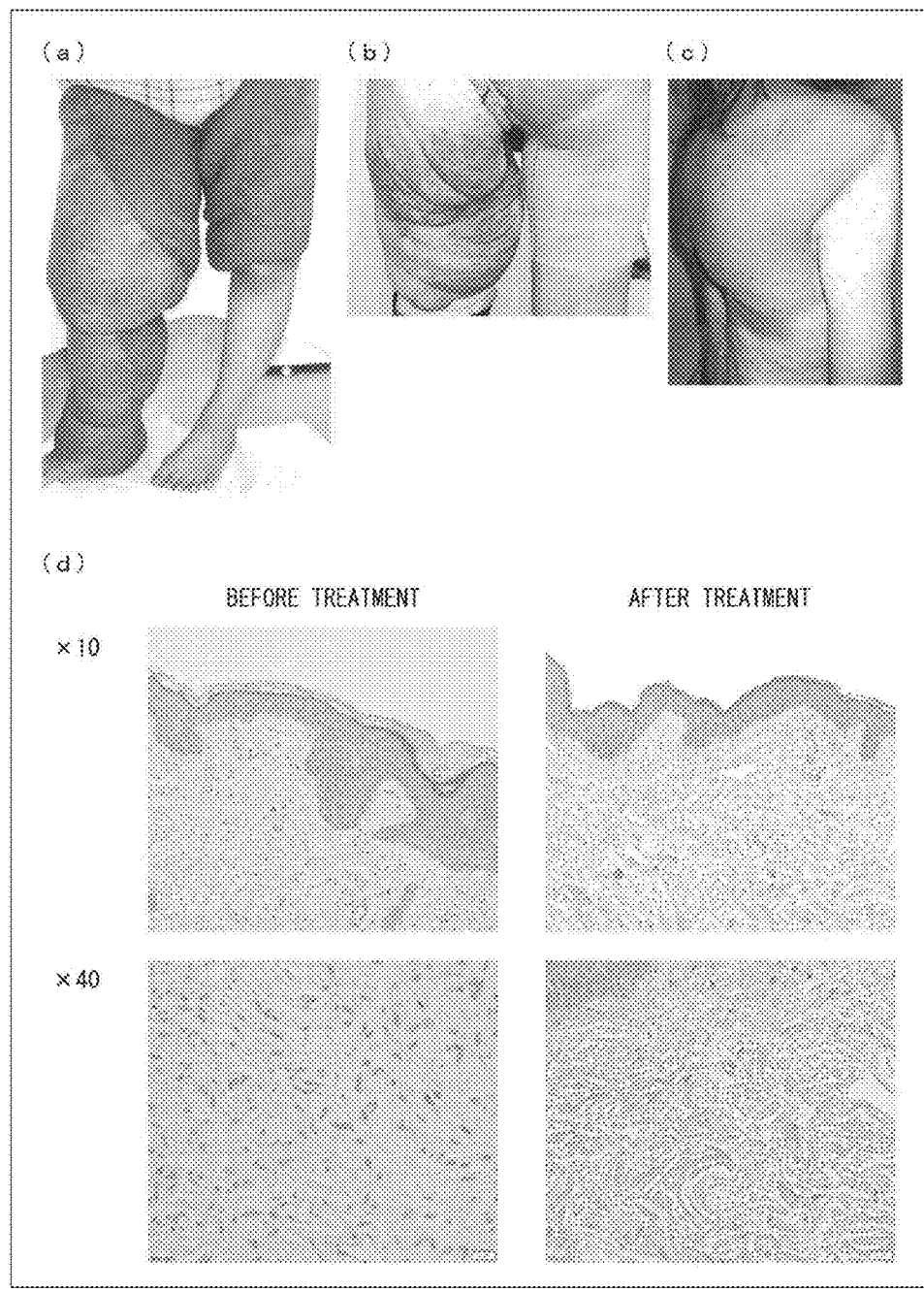

5 Claims, 6 Drawing Sheets mas, diffuse plexiform neurofibromas, nodular plexiform neurofibromas, and malignant peripheral nerve sheath tumors (NPNST).

EXTERNAL MEDICINE FOR DIFFUSE PLEXIFORM NEUROFIBROMA

TECHNICAL FIELD

The present invention relates to an external medicine for diffuse plexiform neurofibromas.

BACKGROUND ART

Neurofibromatosis is a disorder which causes various abnormalities in many organs (e.g., skin and nerves) of a living body.

There are various types of neurofibromatosis. Examples of such types of neurofibromatosis include neurofibromatosis type 1 (NF1, Recklinghausen's disease) and neurofibromatosis type 2 (NF2). Nneurofibromatosis type 1 and neurofibromatosis type 2 are separate disorders having different causes, respectively. For example, neurofibromatosis type 1 has been found to be an autosomal dominant genetic disorder caused by an abnormality in the NF1 gene on chromosome 17.

Symptoms appearing on living bodies are largely different between neurofibromatosis type 1 and neurofibromatosis type 2. For example, neurofibromatosis type 1 causes symptoms such as neurofibromas, cafe-au-lait spots, bone abnormalities, and optic gliomas. Particularly, severe symptoms of neurofibromatosis type 1 appear on the skin. On the other hand, neurofibromatosis type 2 causes symptoms such as acoustic nerve tumors. As compared with symptoms of neurofibromatosis type 1, symptoms of neurofibromatosis type 2 more often appear as central nerve tumors but less often appear on the skin. Further, neurofibromatosis type 1 is often associated with various complications such as pheochromocytomas, gastrointestinal stromal tumors (GISTs) or vascular malformations, which makes treatment of neurofibromatosis type 1 difficult.

Patent Literature 1 discloses a gel composition and an ointment composition each containing at least one of sirolimus and sirolimus derivatives. Though Non-Patent Literature 1 discloses use of sirolimus for internal use in treatment of neurofibromas in neurofibromatosis type 1, therapeutic effects have not been obtained by such use of sirolimus.

Neurofibromas, which are one symptom of neurofibromatosis, have various types, each of which is a separate disorder medically distinguished from another type of neurofibromas and has a unique characteristic. Examples of such types of neurofibromas include cutaneous neurofibro- Diffuse plexiform neurofibromas are fibromas which appear on approximately 10% of patients who developed neurofibromas. A giant diffuse plexiform neurofibroma with a surface having massive folds is flaccid and may be overhanging like a tongue. A diffuse plexiform neurofibroma extending all over a lower limb may exhibit a state of megalomelia, in a case where (a) the diffuse plexiform neurofibroma is found to have infiltrated under the skin into subcutaneous adipose tissue and muscle and (b) osteohypertrophy and bone enlargement are also found. Depending on the locations of affected sites, diffuse plexiform neurofibromas are recognized as hemifacial hypertrophy, blepharoptosis, megalomelia, and the like. In a case where a diffuse plexiform neurofibroma occurs on the face, even a small diffuse plexiform neurofibroma frequently causes a problem such as vision disturbance caused by a tumor mass of an upper eyelid, or nasal deformity (see (a) to (c) of FIG. 1).

Further, a diffuse plexiform neurofibroma is abundant in blood vessels and fragile in tissue, and accordingly may form a giant hematoma from a minor bruise. Such a giant hematoma may be formed suddenly within a short period of time or may be formed as a result of gradual growth of hematoma over several days. Once such a hematoma starts to bleed, hemostasis is difficult because of bleeding from many small blood vessels. There are cases in which bleeding from such a hematoma resulted in a shock or a death due to loss of a large amount of blood.

There is no particular frequent site of cutaneous neurofibromas. In cases where cutaneous neurofibromas occur all over a patient's body, innumerable cutaneous neurofibromas occur mainly on a body trunk and all over the patient's body. Such tumors are soft tumors varying in size and shape and each having a normal-color or pink surface. Among cutaneous neurofibromas, some cutaneous neurofibromas protrude so as to have a hemisphere shape. The number of cutaneous neurofibromas considerably differs depending on each case, and may reach several tens in some cases or may be countless in some other cases.

Nodular plexiform neurofibromas are neurofibromas originating from the perineurium of peripheral nerve and appear on any part of a whole body. That is, nodular plexiform neurofibromas appear on various sites, for example, around the brain, around the spinal cord, in the pelvic cavity, and under the skin. Nodular plexiform neurofibromas located at a shallow part of the skin each appear, along the length of a nerve, as a spindle-shaped tumor that is relatively apparently-circumscribed under the skin and felt elastic hard. These nodular plexiform neurofibromas may be in a continuous beaded form or may form an agglomerate to be one large tumor mass.

Diffuse plexiform neurofibromas may cause loss of a lot of blood from a minor trauma or may become an origin of a malignant tumor (e.g., glioblastoma and malignant peripheral nerve sheath tumor (MPNST), etc.). Therefore, there are demands for rapid development of a medicine and a treatment method, each of which is effective for diffuse plexiform neurofibromas.

CITATION LIST

Patent Literature

[Patent Literature 1] WO2012/105521 A1 (Publication Date: Aug. 9, 2012)

Non-Patent Literature

[Non-Patent Literature 1] Brian Weiss et. al., Pediatr Blood Cancer 2014, 61, 982-986

SUMMARY OF INVENTION

Technical Problem

When a neurofibroma is to be treated, a medicine and a treatment method suitable for the neurofibroma to be treated need to be selected since neurofibromas have widely varying characteristics depending on types, respectively.

In a case where the size of a neurofibroma is small or a boundary between a neurofibroma and normal tissue is relatively apparent, the neurofibroma is surgically resectable. However, since diffuse plexiform neurofibromas are abundant in blood vessels and highly infiltrating, a boundary between a tumor and normal tissue is not apparent and moreover, the tumor and blood vessels or nerves are intricately-intertwined with each other. This makes it difficult to treat diffuse plexiform neurofibromas by surgical operations. This is one problem. Particularly, in a case where a diffuse plexiform neurofibroma becomes gigantic, such a diffuse plexiform neurofibroma makes it difficult to even move a body because of that heavy tumor. In a case where a lower limb has a giant tumor, lower limb amputation may become necessary. There is presently no established medicine or treatment method effective for diffuse plexiform neurofibromas which have become gigantic.

Further, there is another problem in that radiotherapy does not effectively work on diffuse plexiform neurofibromas.

Meanwhile, though an attempt to treat diffuse plexiform neurofibromas with use of an oral medicine has been made, there is no report made on an oral medicine whose significant therapeutic effect has been confirmed.

On the other hand, no attempt to treat diffuse plexiform neurofibromas with use of an external medicine has been made due to the following preconceived ideas (i) and (ii):
(i) external medicines, particularly, external medicines made of a substance, like sirolimus, having a high molecular weight have a low efficiency of active ingredient delivery to a site affected by a diffuse plexiform neurofibroma (in other words, thickened skin tissue); and
(ii) a method of treating a giant fibroma with use of an external medicine is ineffective, and it is a treatment method with use of an oral medicine that is effective as a treatment method for a giant fibroma.

The present invention is attained in view of the above conventional problems, and an object of the present invention is to provide an external medicine capable of treating diffuse plexiform neurofibromas.

Solution to Problem

In view of the above problems, the inventors of the present invention have made diligent studies and as a result, have found that diffuse plexiform neurofibromas can be treated by applying, to the diffuse plexiform neurofibromas, an external medicine containing sirolimus or a sirolimus derivative. The inventors have consequently accomplished the present invention. Further, the inventors of the present invention have found the following (a) to (d) with regard to sirolimus and sirolimus derivatives, so that the inventors of the present invention have accomplished the present invention.
(a) In the case of an orally-administered medicine, though the blood concentration of an active ingredient increases, the concentration of the active ingredient in skin tissue (in other words, sites affected by diffuse plexiform neurofibromas) does not easily reach a therapeutically-effective concentration;
(b) in a case where the concentration of an active ingredient in skin tissue is to be increased to a therapeutically-effective concentration with use of an orally-administered medicine, a large amount of the orally-administered medicine needs to be administered to a patient, and accordingly, this case has an increased risk of systemic side effects;
(c) in the case of an external medicine, though the concentration of an active ingredient in skin tissue (local) increases to a therapeutically-effective concentration, the active ingredient does not easily transfer into blood; and
(d) use of an external medicine containing alcohol allows an active ingredient contained in the external medicine to be more efficiently absorbed into skin tissue.

In order to solve the above problems, an external medicine for diffuse plexiform neurofibromas in accordance with an embodiment of the present invention contains, as an active ingredient, at least one selected from the group consisting of sirolimus and sirolimus derivatives.

The external medicine for diffuse plexiform neurofibromas in accordance with an embodiment of the present invention is preferably a gel.

The external medicine for diffuse plexiform neurofibromas in accordance with an embodiment of the present invention preferably contains ethanol.

The external medicine for diffuse plexiform neurofibromas in accordance with an embodiment of the present invention is preferably arranged such that the ethanol is contained in an amount of 20 wt % to 60 wt %.

The external medicine for diffuse plexiform neurofibromas in accordance with an embodiment of the present invention is preferably arranged such that the active ingredient is contained in an amount of 0.2 wt % to 0.8 wt %.

Advantageous Effects of Invention

An external medicine in accordance with an embodiment of the present invention is capable of treating diffuse plexiform neurofibromas for which neither an effective therapeutic agent nor an effective treatment method has been established. In particular, the external medicine shrinks an inoperable diffuse plexiform neurofibroma which has become gigantic, and the external medicine consequently improves QOL of patients remarkably. Further, the external medicine can prevent hematoma formation or loss of a large amount of blood from a bruise or the like. An early start of treatment makes it possible to prevent a tumor from becoming a giant tumor.

An external medicine in accordance with an embodiment of the present invention is absorbed at a high absorption rate, so that an active ingredient of the external medicine can be efficiently delivered to skin tissue and muscle tissue which are affected sites.

An external medicine in accordance with an embodiment of the present invention can keep a local concentration of an active ingredient in skin tissue, muscle tissue, or the like high, but an amount of the active ingredient absorbed and transferred into blood is small. The external medicine is therefore a safe preparation that has a low risk of the occurrence of systemic side effects.

An external medicine in accordance with an embodiment of the present invention can be used for external application which is, unlike systemic administration, application only to a limited lesion area.

BRIEF DESCRIPTION OF DRAWINGS (a) to (c) of FIG. 1 are photographs showing symptoms of diffuse plexiform neurofibromas; and (d) of FIG. 1 includes photographs showing a histological change of diffuse plexiform neurofibroma before and after administration of an external medicine in accordance with an example of the present invention.

Figure 2:
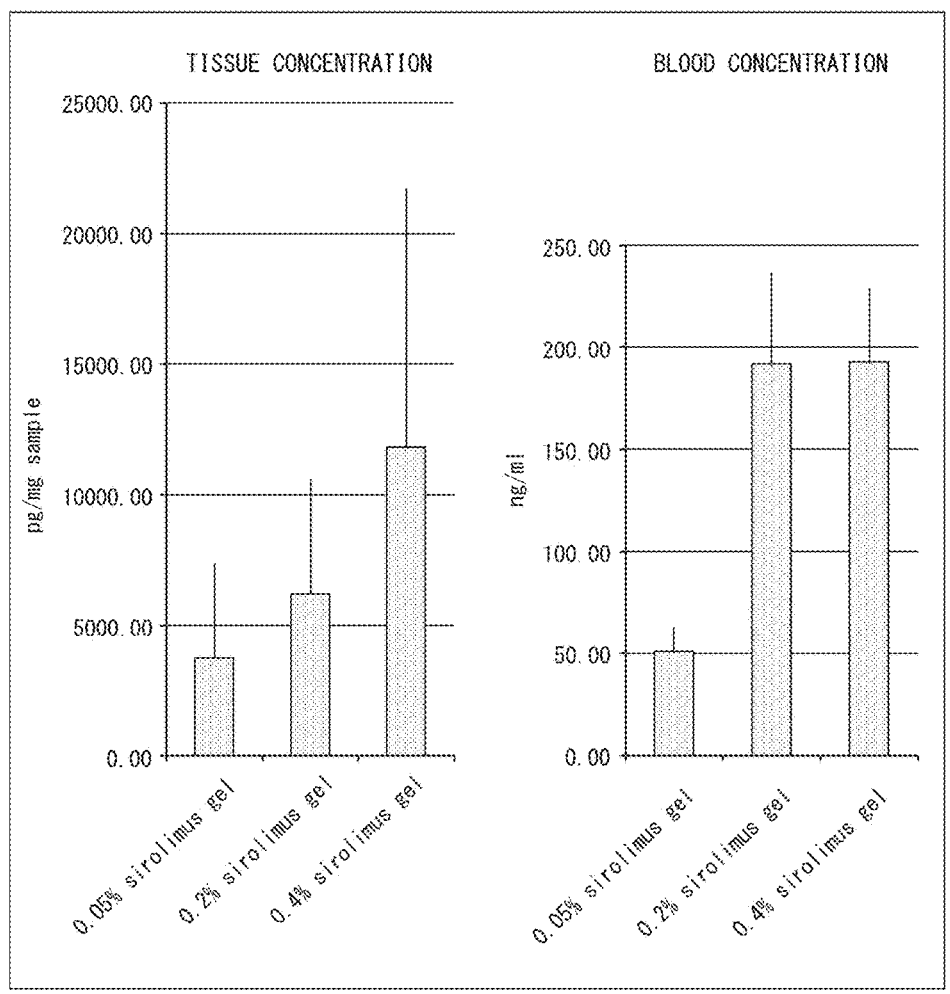

FIG. 2 includes graphs showing measurement results of sirolimus concentration in tissue and sirolimus concentrations in blood after administration of an external medicine in accordance with an example of the present invention.

Figure 3:
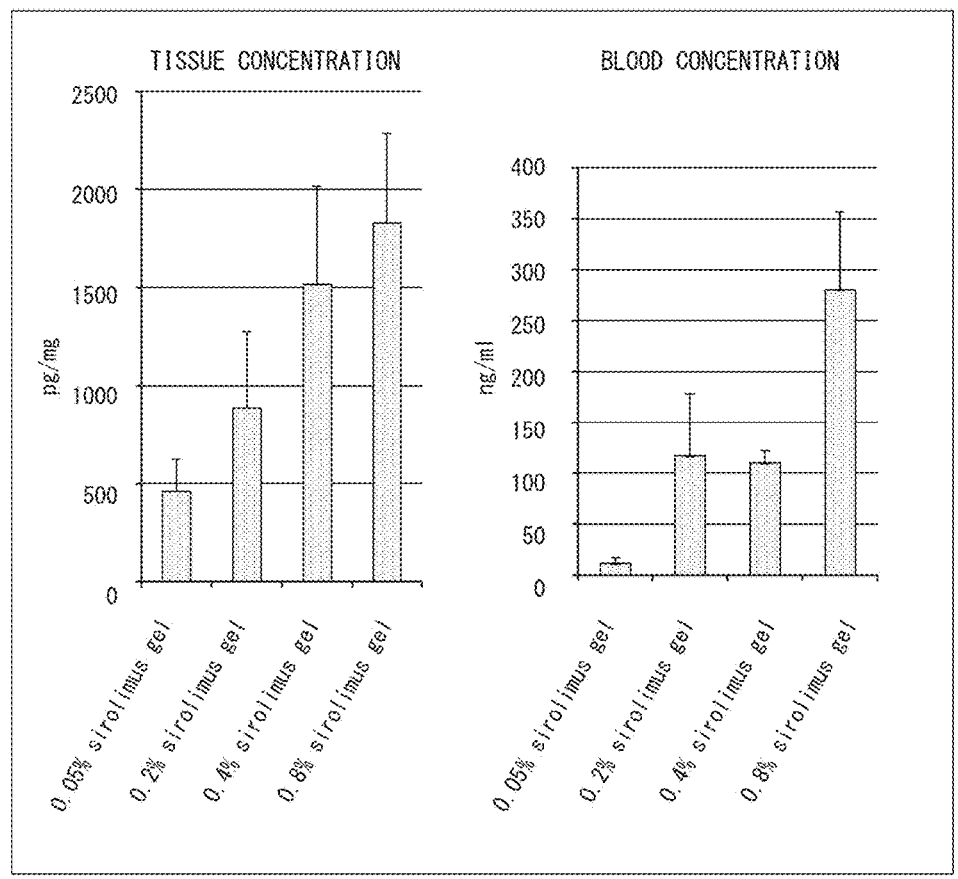

FIG. 3 includes graphs showing measurement results of sirolimus concentration in tissue and sirolimus concentrations in blood after administration of an external medicine in accordance with an example of the present invention.

Figure 4:
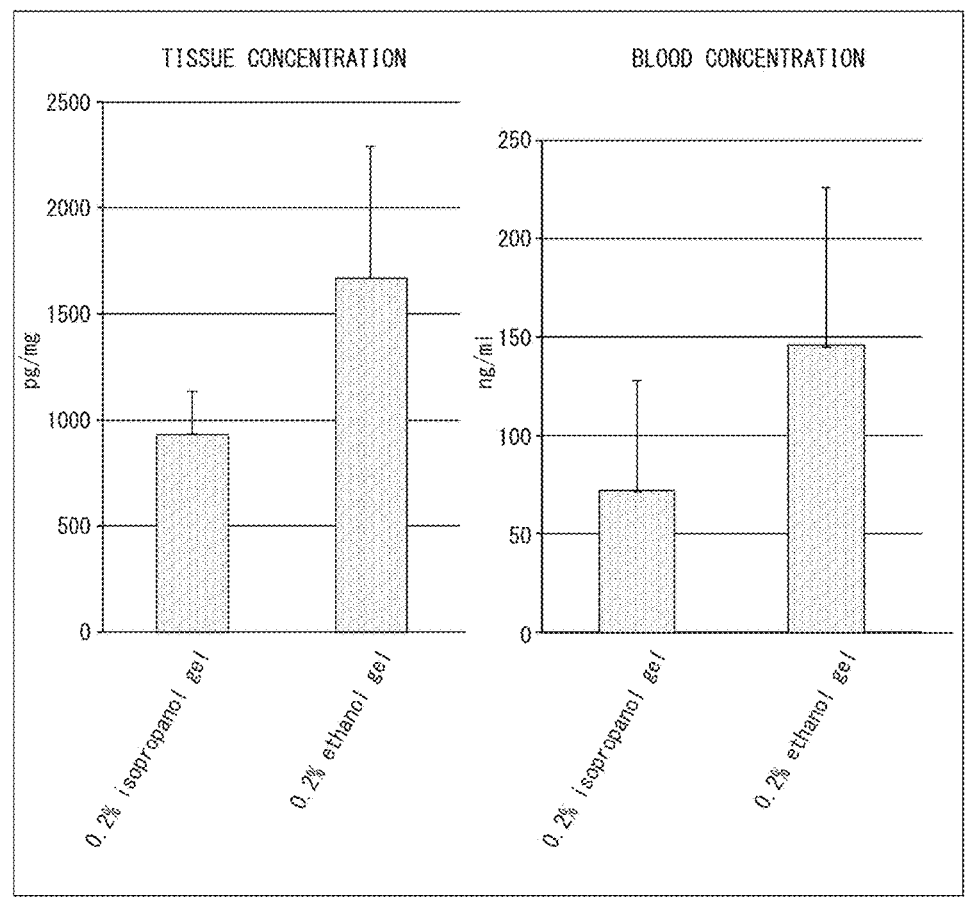

FIG. 4 includes graphs showing measurement results of sirolimus concentration in tissue and sirolimus concentrations in blood after administration of an external medicine in accordance with an example of the present invention.

Figure 5:
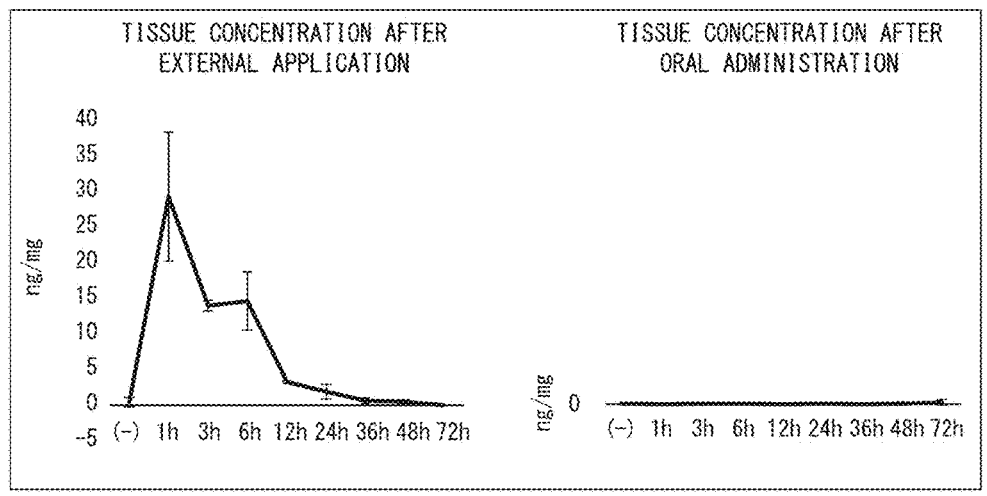

FIG. 5 includes graphs for comparison between (a) sirolimus concentration in tissue in the case of single administration of an external medicine in accordance with an example of the present invention and (b) sirolimus concentration in tissue in the case of single administration of an oral medicine.

Figure 6:
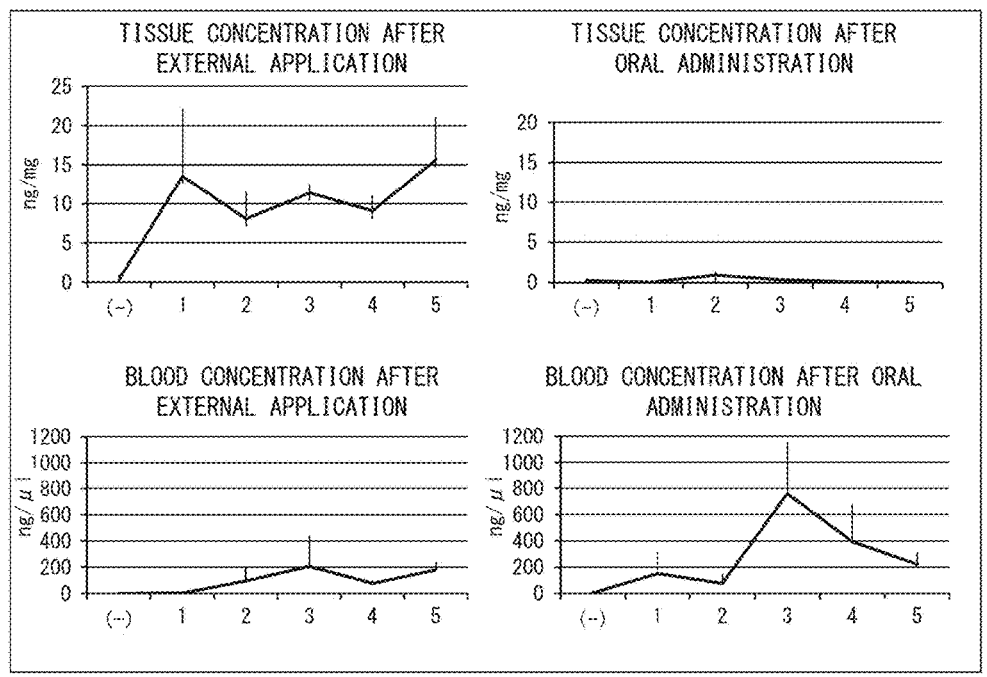

FIG. 6 includes graphs for comparing (a) sirolimus concentration in tissue and sirolimus concentration in blood in the case of repeated administration of an external medicine in accordance with an example of the present invention with (b) sirolimus concentration in tissue and sirolimus concentration in blood in the case of repeated administration of an oral medicine.

Figure 7:
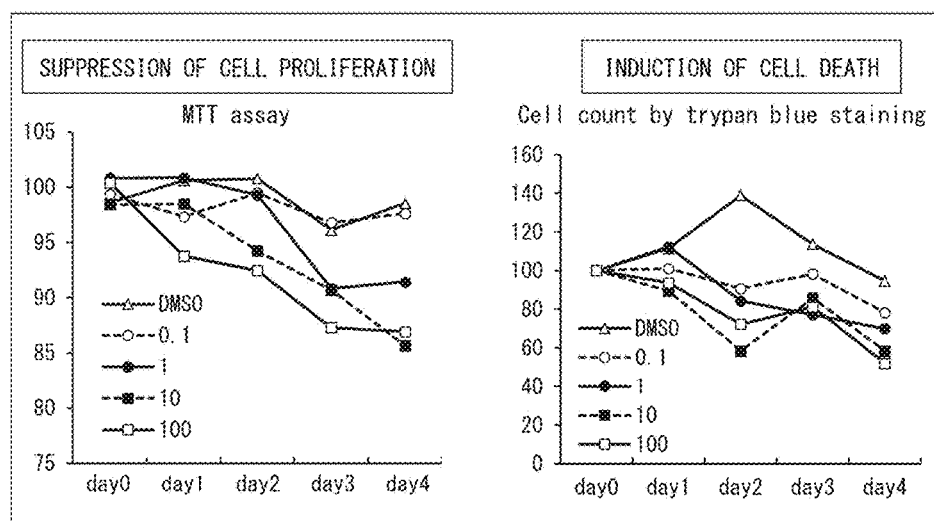

FIG. 7 includes graphs showing, respectively, (a) a result of analyzing cell proliferation by an MTT assay method and (b) a result of analyzing cell death by the trypan blue cell counting method, in an example of the present invention.

DESCRIPTION OF EMBODIMENTS

The following description will discuss an embodiment of the present invention. However, the present invention is not limited to the embodiment. The present invention is not limited to any of configurations described below, and can be altered in many ways within the scope of the claims. An embodiment and/or an example derived from a proper combination of technical means disclosed in different embodiments and/or examples are/is also encompassed in the technical scope of the present invention. In addition, all of the academic document and patent literature listed herein are incorporated by reference herein. Note that a numerical range "A to B" herein means "not less than A and not more than B" unless otherwise specified.

An external medicine in accordance with an embodiment of the present invention is an external medicine for a medical procedure and/or a medical treatment for diffuse plexiform neurofibromas, the external medicine containing, as an active ingredient, at least one selected from the group consisting of sirolimus and sirolimus derivatives.

Sirolimus (also known as rapamycin) and sirolimus derivatives have been already used for treatment of other diseases and accordingly, safety in clinical practice of sirolimus and sirolimus derivatives has been confirmed. Therefore, use of sirolimus and sirolimus derivatives makes it possible to provide a safer external medicine for diffuse plexiform neurofibromas.

Such a sirolimus derivative is not limited to a particular one, and can be for example, everolimus, temsirolimus, ridaforolimus, or zotarolimus. These derivatives are each known to have a basic skeleton which is substantially the same as that of sirolimus, and to have a bioactivity equivalent to that of sirolimus. These sirolimus derivatives each, like sirolimus, can be therefore used as the active ingredient of the external medicine in accordance with the present embodiment. From the viewpoint of easy preparation of the external medicine, among the above substances, preferably, sirolimus and/or everolimus is/are used. Further, among the above substances, it is more preferable to use rapamycin whose percutaneous absorption has been confirmed, as compared to everolimus etc. whose percutaneous absorption is considered difficult because of a normally large molecular weight and a water-soluble property of everolimus etc.

Though the active ingredient contained in the external medicine in accordance with the present embodiment is not particularly limited in amount, the external medicine in accordance with the present embodiment allows the active ingredient to be efficiently absorbed into skin tissue. Further, the external medicine in accordance with the present embodiment can makes it possible to deliver the active ingredient to thickened skin tissue that is affected by diffuse plexiform neurofibromas.

Examples of the amount of the active ingredient contained in the external medicine in accordance with the present embodiment can be 0.05 wt % to 1.0 wt %, 0.1 wt % to 0.9 wt %, 0.2 wt % to 0.8 wt % (or not less than 0.2 wt % and less than 0.8 wt %), 0.3 wt % to 0.7 wt %, 0.35 wt % to 0.6 wt %, 0.4 wt % to 0.6 wt %, or 0.4 wt % to 0.5 wt %, relative to a total weight of the external medicine.

From the viewpoint of (i) preventing systemic side effects by suppressing transfer of the active ingredient into blood as much as possible and at the same time, (ii) obtaining therapeutic effects by increasing the concentration of the active ingredient in skin tissue to a therapeutically-effective concentration, the amount of the active ingredient contained in the external medicine in accordance with the present embodiment is preferably 0.2 wt % to 0.8 wt % (or not less than 0.2 wt % and less than 0.8 wt %), more preferably 0.3 wt % to 0.7 wt %, and more preferably 0.4 wt % to 0.6 wt %, relative to the total weight of the external medicine.

The external medicine in accordance with the present embodiment is used in a medical procedure (in other words, prevention of symptom exacerbation) and/or a medical treatment for diffuse plexiform neurofibromas. Examples of diffuse plexiform neurofibromas for which the external medicine in accordance with the present embodiment is used can be a diffuse plexiform neurofibroma developed in association with neurofibromatosis type 1.

The external medicine in accordance with the present embodiment can be used not only for humans but also for non-human animals. Examples of the non-human animals include mammals excluding humans. The mammals excluding humans include, for example, cloven-hoofed animals such as cattle, boars, pigs, sheep, and goats, ungulates such as horses, rodents such as mice, rats, hamsters, and squirrels, lagomorphs such as rabbits, carnivorous animals such as dogs, cats, and ferrets, and the like. Further, these non-human animals are not limited to barn animals or companion animals (pet animals) and can be wild animals.

An amount of the external medicine in accordance with the present embodiment to be applied per unit surface area of a living body is not particularly limited, and can be 0.001 g/cm$^2$ to 0.01 g/cm$^2$, 0.002 g/cm$^2$ to 0.009 g/cm$^2$, 0.003 g/cm$^2$ to 0.008 g/cm$^2$, 0.004 g/cm$^2$ to 0.007 g/cm$^2$, or 0.005 g/cm$^2$ to 0.006 g/cm$^2$.

The external medicine in accordance with the present embodiment should be applied in the above amount once every day or once every two or three days. It is preferable to apply the external medicine every day. In a case where the above medicine is applied every day, the external medicine is applied preferably 1 time to 3 times a day, more preferably 2 times to 3 times a day, and most preferably 2 times a day.

The external medicine in accordance with the present embodiment not only allows for an effective medical procedure and/or an effective medical treatment for diffuse plexiform neurofibromas, but also makes it possible to prevent the occurrence of side effects.

The external medicine in accordance with the present embodiment may be in a formulation such as a gel, an ointment, a liniment, a lotion, a cream, or the like.

For example, i) a gel can be prepared by gelatinization of a solution containing the active ingredient; ii) an ointment can be prepared by mixing an ointment base with the active ingredient; and iii) a poultice, a liniment, a lotion, and a cream can be each prepared by a well-known method. Note that as compared to an ointment, a gel is more preferable formulation since the active ingredient in a gel is easily absorbed into skin tissue.

The following will describe one concrete configuration example of gels and one concrete configuration example of ointments. An embodiment of the present invention, however, is not limited to these configurations.

(A) Gel

As described above, the external medicine in accordance with the present embodiment may be a gel which can be obtained by gelatinization of a solution containing the active ingredient.

When a gel is prepared, a solution containing the active ingredient should be gelatinized with use of a gelling agent. Examples of the gelling agent include a carboxy vinyl polymer, carboxymethyl cellulose, aluminum hydroxide, bentonite, and the like.

A concrete configuration of the carboxy vinyl polymer is not limited to a particular one, and can be Carbopol (registered trademark), HIVISWAKO (registered trademark), or AQUPEC (registered trademark). From the viewpoint of the feel of the external medicine in a case where the external medicine is applied, among others, Carbopol (registered trademark) 934P NF or Carbopol (registered trademark) 980 is preferable.

In a case where Carbopol (registered trademark) is used, a pH adjuster (e.g., tris(hydroxymethyl)aminomethane or triethanolamine) is added to a solution containing Carbopol (registered trademark), so as to adjust the pH of the solution to a neutral pH and thereby to gelatinize the solution.

The external medicine in accordance with the present embodiment preferably contains alcohol. Alcohol can cause the active ingredient contained in the external medicine to be efficiently absorbed into skin tissue and consequently to be efficiently delivered to an affected site. Examples of such alcohol include ethanol and isopropanol. From the viewpoint of more efficient absorption of the active ingredient into skin tissue, ethanol is more preferable as the alcohol.

The alcohol contained in the external medicine in accordance with the present embodiment is not particularly limited in amount, and the amount of the alcohol contained is 10 wt % to 70 wt %, 20 wt % to 70 wt %, 30 wt % to 70 wt %, 40 wt % to 70 wt %, 45 wt % to 70 wt %, 50 wt % to 70 wt %, 55 wt % to 70 wt %, 60 wt % to 70 wt %, 10 wt % to 60 wt %, 20 wt % to 60 wt %, 30 wt % to 60 wt %, 40 wt % to 60 wt %, 45 wt % to 60 wt %, 10 wt % to 55 wt %, 20 wt % to 55 wt %, 30 wt % to 55 wt %, 40 wt % to 55 wt %, 45 wt % to 55 wt %, 10 wt % to 50 wt %, 20 wt % to 50 wt %, 30 wt % to 50 wt %, 40 wt % to 50 wt %, or 45 wt % to 50 wt %, relative to the total weight of the external medicine. Preferably, the amount of the alcohol contained is 20 wt % to 60 wt %.

The amount of the alcohol must be an amount which allows sirolimus to be sufficiently dissolved in the alcohol, and accordingly the amount of the alcohol is preferably not less than 20 wt %. In order to prepare a gel having a concentration at which a therapeutic effect can be expected, the amount of the alcohol is preferably not less than 30 wt % relative to a gel weight, and more preferably not less than 40 wt % relative to the gel weight. In a case where the amount of the alcohol is more than 60 wt %, the alcohol easily evaporates from a resultant preparation. This makes it difficult to store (preserve) the preparation in a manner that the preparation keeps a stable active ingredient concentration. The amount of the alcohol is therefore more preferably approximately 50 wt % (45 wt % to 55 wt %). When the external medicine contains the alcohol in an amount that allows the active ingredient to be sufficiently dissolved in the alcohol, the active ingredient can be more effectively absorbed into skin tissue. In a case where the external medicine contains the alcohol in an amount of not more than 50 wt %, a larger amount of the alcohol results in more sufficient dissolution of the active ingredient and consequently in more efficient absorption of the external medicine into skin tissue.

The amount of the gelling agent contained in the gel is not particularly limited, and only needs to be an amount sufficient to gelatinize the solution containing the active ingredient. The amount of the gelling agent contained in the gel can be, for example, not less than 1.5 wt % (more specifically, 1.5 wt % to 20 wt %, 1.5 wt % to 15 wt %, 1.5 wt % to 10 wt %, 1.5 wt % to 5 wt %, or 1.5 wt % to 2.5 wt %), relative to a total weight of the gel.

The amount of the pH adjuster (neutralizer) contained in the gel is not particularly limited, and can be set as appropriate in accordance with respective amounts of a solvent and the gelling agent. The amount of the pH adjuster contained in the gel can be, for example, 0.5 wt % to 5.0 wt %, 0.5 wt % to 2.5 wt %, or 0.5 wt % to 1.0 wt %, relative to the total weight of the gel.

More specifically, in a case where a gelling agent such as Carbopol (registered trademark) 934P NF and a pH adjuster such as tris(hydroxymethyl)aminomethane are used, the amount of the gelling agent may be 1.6 wt % relative to the total weight of the gel and the amount of the pH adjuster may be 0.4 wt %, 0.6 wt % or 0.8 wt % relative to the total weight of the gel. Certainly, an embodiment of the present invention is not limited to the above ratios.

The amount of the active ingredient contained in the gel is not particularly limited, and can be an amount described earlier as the "amount of the active ingredient contained in the external medicine".

The gel may contain another component(s) in addition to the active ingredient, the solvent (alcohol), the gelling agent and the pH adjuster (neutralizer) which have been described above. Examples of such another component(s) include a water-soluble polymer and a desired active ingredient other than the above-described active ingredient(s).

Examples of the water-soluble polymer include polyethyleneglycol, starch, methylcellulose, hydroxypropylcellulose (HPC), polyvinyl alcohol, polyvinyl methyl ether, polyvinyl pyrrolidone, and the like. In a case where the gel contains hydroxypropylcellulose, the viscosity of the gel can be increased. In other words, containing hydroxypropylcellulose in the gel allows the gel to more easily stay on the skin.

The amount of the another component(s) contained in the gel is not particularly limited, and can be, for example, not more than 50 wt %, not more than 40 wt %, not more than 30 wt %, not more than 20 wt %, not more than 10 wt %, not more than 5 wt %, or not more than 1 wt %, relative to the total weight of the gel.

(B) Ointment

As described above, the external medicine in accordance with the present embodiment may be an ointment containing a base and the active ingredient.

An amount of the active ingredient contained in the ointment is not particularly limited and can be an amount described above as the "amount of the active ingredient contained in the external medicine". The amount has been described above and therefore a concrete description thereof will be omitted here.

Examples of the base include waxes (e.g., natural waxes such as white beeswax, lanolin, carnauba wax, and spermaceti wax, mineral waxes such as montan wax, synthetic waxes, etc.), paraffins (e.g., liquid paraffin, solid paraffin, etc.), petrolatum (e.g., white petrolatum, yellow petrolatum, etc.), and the like.

The amount of the base contained in the ointment is not particularly limited, and can be, for example, not less than 10 wt %, not less than 20 wt %, not less than 30 wt %, not less than 40 wt %, not less than 50 wt %, not less than 60 wt %, not less than 70 wt %, not less than 80 wt %, or not less than 90 wt %, relative to a total weight of the ointment, The ointment can contain propylene carbonate, solid paraffin and white petrolatum. Moreover, the ointment can further contain liquid paraffin in addition to propylene carbonate, solid paraffin and white petrolatum. Furthermore, the ointment can further contain white beeswax in addition to propylene carbonate, solid paraffin, white petrolatum and liquid paraffin.

The ointment can be produced according to a well-known method. The following describes one example of a production method of the ointment.

The ointment can be prepared by using, for example, a homomixer (for example, manufactured by PRIMIX Corporation) or a universal mixer (for example, manufactured by Dalton Corporation). In a case where the base is solid at room temperature, the base should be heated until the base liquefies, and then the base in a liquid state should be mixed with a solution in which the active ingredient is dissolved. For example, the ointment can be produced by: (i) melting various components (e.g., waxes, paraffins, petrolatums, etc.) that are solid at room temperature by heating the components to a temperature (e.g., 70° C.) higher than melting points of the components; (ii) adding, to the components thus melted, a solution in which the active ingredient is dissolved, and stirring a mixture thus obtained; and (iii) then cooling the mixture to a temperature (e.g., 40° C.) around room temperature, concurrently with stirring.

Another method of producing the ointment includes the steps of: melting an entire base at a temperature of 70° C. to 80° C.; stirring, by use of a planetary centrifugal mixer (manufactured by Thinky Corporation) in a stirring mode, the base first at 800 rpm for 30 minutes, next at 1000 rpm for 5 minutes, and subsequently at 2000 rpm for 1 minute (15° C.); adding, to the base, a solution in which the active ingredient is dissolved; and further stirring at 1000 rpm for 1 minute and then at 2000 rpm for 1 minute (without cooling). Such another method makes it possible to prepare a good-quality ointment in which very fine particles containing the active ingredient are further dispersed.

In a case where the ointment contains the another component(s) described above, the ointment should be prepared by: (i) preparing a solution in which the active ingredient and the another components(s) are dissolved in a desired solvent; (ii) adding a base to the solution; and (iii) carrying out steps subsequent to the step (ii), according to the method which has been described above.

EXAMPLES

<1. Preparation of External Medicine>

First, after sirolimus (rapamycin) was added to ethanol or isopropanol and dissolved in the ethanol or isopropanol, water (specifically, water for injection) was further added and mixed, so that a mixed solution was prepared. Next, to this mixed solution, Carbopol (registered trademark) (specifically, Carbopol (registered trademark) 934P NF) was added and mixed. As a result, a uniform suspension was prepared. To the suspension, a neutralizer (specifically, tris(hydroxymethyl)aminomethane was added and mixed, so that gels (external medicines 1 to 9) were prepared. Tables 1 and 2 below show gel compositions.

Meanwhile, all of white beeswax, liquid paraffin, solid paraffin, and white petrolatum were weighed and put in one container. Then, a mixture in the container was melted at a temperature of 70° C. to 80° C., and stirred, by use of a planetary centrifugal mixer (manufactured by Thinky Corporation) in a stirring mode, first at 800 rpm for 30 minutes, next at 1000 rpm for 5 minutes, and subsequently at 2000 rpm for 1 minute (15° C.). To this melted material, added was a solution in which sirolimus was dissolved in propylene carbonate in a hot-water bath at a temperature of 60° C. to 70° C. Then, a mixture thus obtained was stirred at 1000 rpm for 1 minute and then at 2000 rpm for 1 minute (without cooling), so that an ointment (external medicine 10) was prepared.

TABLE 1

| | Sirolimus Concentration [%] | Sirolimus Content [mg] | Carbopol 934P NF Content [mg] | Ethanol Content [mg] | Tris[hydroxymethyl] aminomethane Content [mg] | Water Content [mg] | Total Amount [mg] |
| --- | --- | --- | --- | --- | --- | --- | --- |
| External Medicine 1 | 0 | 0 | 16 | 488 | 6 | 490 | 1000 |
| External Medicine 2 | 0.05 | 0.5 | 16 | 487.5 | 6 | 490 | 1000 |
| External Medicine 3 | 0.1 | 1 | 16 | 487 | 6 | 490 | 1000 |
| External Medicine 4 | 0.2 | 2 | 16 | 486 | 6 | 490 | 1000 |
| External Medicine 5 | 0.8 | 8 | 16 | 480 | 6 | 490 | 1000 |

TABLE 2

| | Sirolimus Concentration [%] | Sirolimus Content [mg] | Carbopol 934P NF Content [mg] | Isopropanol Content [mg] | Tris[hydroxymethyl] aminomethane Content [mg] | Water Content [mg] | Total Amount [mg] |
| --- | --- | --- | --- | --- | --- | --- | --- |
| External Medicine 6 | 0.05 | 0.5 | 16 | 487.5 | 6 | 490 | 1000 |
| External Medicine 7 | 0.2 | 2 | 16 | 486 | 6 | 490 | 1000 |

TABLE 2-continued

|  | Sirolimus Concentration [%] | Sirolimus Content [mg] | Carbopol 934P NF Content [mg] | Isopropanol Content [mg] | Tris[hydroxymethyl] aminomethane Content [mg] | Water Content [mg] | Total Amount [mg] |
|---|---|---|---|---|---|---|---|
| External Medicine 8 | 0.4 | 4 | 16 | 484 | 6 | 490 | 1000 |
| External Medicine 9 | 0.8 | 8 | 16 | 480 | 6 | 490 | 1000 |

TABLE 3

|  | Sirolimus Concentration [%] | Sirolimus Content [mg] | Propylene Carbonate Content [mg] | White Beeswax Content [mg] | Liquid Paraffin Content [mg] | Solid Paraffin Content [mg] | White Petrolatum Content [mg] | Total Amount [mg] |
|---|---|---|---|---|---|---|---|---|
| External Medicine 10 | 0.2 | 2 | 58 | 5 | 10 | 30 | 895 | 1000 |

<2. Efficacy of External Medicine for Diffuse Plexiform Neurofibromas>

The external medicine 4 was applied for 12 weeks to diffuse plexiform neurofibromas on patients (three patients) suffering from neurofibromatosis type 1. Specifically, the external medicine 4 was applied, to the diffuse plexiform neurofibromas, once a day and each time in an amount of 1 g per 300 cm$^2$ of area affected by diffuse plexiform neurofibromas. After 84 days from the start of application of the external medicine 4, a sirolimus concentration in tissue and a sirolimus concentration in blood were measured. Further, a state of tissue was checked by tissue staining. In addition, whether each of the patients had subjective symptoms was checked.

Table 4 and (d) of FIG. 1 show results of the above test. In Table 4 below, the sign "-" in the column of "Sirolimus Concentration in Blood" and in the column of "Sirolimus Concentration in Tissue" indicates that the concentration is not more than a measurement limit (1 ng/mL or 1 ng/mg). Meanwhile, the sign "-" in the column of "Patient's Subjective Symptoms" indicates that there was no change in subjective symptoms. Note that the "Sirolimus Concentration in Blood" was measured in a hospital laboratory, by using ARCHITECT (registered trademark) Sirorimus, ARCHITECT (registered trademark) Sirorimus Calibrator, and ARCHITECT (registered trademark) Sirorimus Whole Blood Precipitation Reagent, while the "Sirolimus Concentration in Tissue" was measured according to LC-ESI/MS method.

It was found that as shown in Table 4, the external medicine in accordance with the present Example can keep the sirolimus concentration in tissue high (at a therapeutically-effective concentration), while suppressing the sirolimus concentration in blood to a low level (in the case of an orally-administered medicine, a sirolimus concentration in blood would be in a range of approximately 5 ng/mL to 10 ng/mL or not less than this range). This indicates that the external medicine in accordance with the present Example is capable of not only effectively treating diffuse plexiform neurofibromas but also preventing side effects.

The test results in the column of "histological observation" in Table 4 is shown in (d) of FIG. 1, separately. Note that (d) of FIG. 1 shows images of stained diffuse plexiform neurofibromas obtained by hematoxylin-eosin staining before and after treatment. Note that in the hematoxylin-eosin staining, a section prepared from a paraffin block was stained with Mayer's hematoxylin produced by Wako Pure Chemical Industries Ltd. and eosin after paraffin had been removed from the section. As a result, histological changes (specifically, decrease in number of cells, and swelling of fibers) were observed in diffuse plexiform neurofibromas before and after the treatment. This indicates that the external medicine in accordance with the present Example advantageously shrinks diffuse plexiform neurofibromas.

Further, as shown in the column of "patient's subjective symptoms" in Table 4, there was a patient who was aware of a change in subjective symptoms that it became easier to put on clothes. This also indicates that the external medicine of the present Example advantageously shrinks diffuse plexiform neurofibromas.

TABLE 4

|  | Patient | Sirolimus Concentration in Blood [ng/mL] | Sirolimus Concentration in Tissue [ng/mg] | Histological Observation | Patient's Subjective Symptoms |
|---|---|---|---|---|---|
| Before Starting Application | Patient A | — | — | Tissues unique to neurofibromas | — |
|  | Patient B | — | — | Tissues unique to neurofibromas | difficult to put on clothes |
|  | Patient C | — | — | Tissues unique to neurofibromas | — |
| 12 Weeks After Starting Application | Patient A | — | 2.6 to 2.8 | Expanded subcutaneaus time in neurofibroma area | — |

TABLE 4-continued

| Patient | Sirolimus Concentration in Blood [ng/mL] | Sirolimus Concentration in Tissue [ng/mg] | Histological Observation | Patient's Subjective Symptoms |
|---|---|---|---|---|
| Patient B | 1.3 | 1.6 to 1.9 | Expanded subcutaneous tissue in neurofibroma area | easy to put on closes |
| Patient C | — | 0.8 to 0.9 | Expanded subcutaneous tissue in neurofibroma area | — |

<3. Sirolimus Concentration in Tissue and Sirolimus Concentration in Blood>

The external medicines 6 to 8 each were applied to BALB/c mice for 12 days. Specifically, each of the external medicines 6 to 8 was applied once a day to BALB/c mice. Note that each of the external medicines 6 to 8 was applied each time in an amount of 100 mg per 10 cm$^2$ of the skin of the BALB/c mice. After 12 days from the start of such application, a sirolimus concentration in tissue and a sirolimus concentration in blood were measured.

Further, the external medicines 6 to 9 each were applied to hairless mice for 3 weeks. Specifically, the external medicines 6 to 9 each were applied once a day to hairless mice. Note that each of the external medicines 6 to 9 was applied each time in an amount of 100 mg per 10 cm$^2$ of the skin of the hairless mice. After 21 days from the start of such application, a sirolimus concentration in tissue and a sirolimus concentration in blood were measured.

FIG. 2 shows test results on the BALB/c mice, while FIG. 3 shows test results on the hairless mice. It was found that as shown in FIGS. 2 and 3, the external medicines in accordance with the present Examples are capable of not only keeping the sirolimus concentration in tissue high (at a therapeutically-effective concentration) but also suppressing the sirolimus concentration in blood to a low level.

Further, as shown in FIGS. 2 and 3, when the sirolimus concentration in external medicine was changed from 0.2% to 0.4%, the sirolimus concentration in tissue significantly increased whereas the sirolimus concentration in blood stayed substantially the same. This indicates that in a case where the sirolimus concentration in external medicine is approximately 0.4% (e.g., 0.2 wt % to 0.8 wt % (or not less than 0.2 wt % and less than 0.8 wt %), preferably 0.3 wt % to 0.8 wt % (or not less than 0.3 wt % and less than 0.8 wt %), more preferably 0.4 wt % to 0.8 wt % (or not less than 0.4 wt % and less than 0.8 wt %)), the sirolimus concentration in tissue can be increased to the highest possible level while the sirolimus concentration in blood can be decreased to the lowest possible level. In other words, the above configuration makes it possible to effectively treat diffuse plexiform neurofibromas while side effects were suppressed to the lowest possible level.

<4. Studies on Alcohol Contained in External Medicines>

The external medicine 4 containing ethanol was applied to some hairless mice for 3 weeks, and the external medicine 7 containing isopropanol was applied to other hairless mice for 3 weeks. Specifically, each of the external medicine 4 and the external medicine 7 was applied to the hairless mice once a day and each time in an amount of 100 mg per 10 cm$^2$ of the skin of the hairless mice. After 21 days from the start of such application, a sirolimus concentration in tissue and a sirolimus concentration in blood were measured.

FIG. 4 shows test results. It was found that as shown in FIG. 4, as compared to the external medicine containing isopropanol, the external medicine containing ethanol advantageously caused more sirolimus to be absorbed into tissue. Further, it was also found that as shown in FIG. 4, the external medicine containing ethanol is also capable of not only keeping the sirolimus concentration in tissue high (at a therapeutically-effective concentration) but also suppressing the sirolimus concentration in blood to a low level.

<5. Comparison Between External Medicine and Oral Medicine (Single Administration)>

External medicine: 15 mg of the external medicine 5 (120 µg of sirolimus in total) was applied one time to the backs of hairless mice. After 1 hour, 3 hours, 6 hours, 12 hours, 24 hours, 36 hours, 48 hours, and 72 hours from that application, a sirolimus concentration in tissue was measured after stratum corneum had been removed from the backs of the hairless mice by tape-stripping the backs of the hairless mice.

Oral medicine: 200 µL of a solution containing sirolimus at a concentration of 250 µg/200 µL was orally administered to mice once. After 1 hour, 3 hours, 6 hours, 12 hours, 24 hours, 36 hours, 48 hours and 72 hours from that oral administration, a sirolimus concentration in tissue was measured after stratum corneum was removed from the backs of the hairless mice by tape-stripping the backs of the hairless mice.

FIG. 5 shows test results. It was found that as shown in FIG. 5, the external medicine can increase the sirolimus concentration in tissue to a much higher level as compared to the oral medicine.

<6. Comparison Between External Medicine and Oral Medicine (Repeated Administration)>

External medicine: 15 mg of the external medicine 5 (120 µg of sirolimus in total) was applied once a day for continuous 5 days to the backs of hairless mice. After 1 day, 2 days, 3 days, 4 days, and 5 days from the start of such repeated application, a sirolimus concentration in tissue and a sirolimus concentration in blood were measured.

Oral medicine: 200 of a solution containing sirolimus at a concentration of 250 µg/200 µL was orally administered to mice once a day for continuous 5 days. After 1 day, 2 days, 3 days, 4 days, and 5 days from the start of such repeated application, a sirolimus concentration in tissue and a sirolimus concentration in blood were measured.

FIG. 6 shows test results. It was found as shown in FIG. 6, that when a sirolimus concentration in tissue in the case of the external medicine was compared with a sirolimus concentration in tissue in the case of the internal medicine on the day on which a sirolimus concentration in blood in the case of the external medicine was substantially equal to a sirolimus concentration in blood in the case of the internal medicine, the sirolimus concentration in tissue in the case of the external medicine was approximately 100 times higher than that in the case of the internal medicine.

<7. Studies on Cell Proliferation-Suppressing Effect of Sirolimus and Cell Death-Inducing Effect of Sirolimus>

According to a well-known method, fibroblasts derived from diffuse plexiform neurofibromas of a patient suffering neurofibromatosis type 1 were cultured. After sirolimus was added, to a culture medium where the fibroblasts were being cultured, such that the final concentration of sirolimus would be 0.1 nM, 1 nM, 10 nM or 100 nM, the fibroblasts were further cultured. Thereafter, cell proliferation and cell death of the fibroblasts were analyzed. Note that DMSO was used as a negative control for studies of sirolimus.

The cell proliferation was analyzed by the MTT assay method. More specifically, the cell proliferation was analyzed with use of Cell Count Reagent SF manufactured by Nacalai tesque, Inc. Meanwhile, the cell death was analyzed by the trypan blue cell counting method. More specifically, the cell death was analyzed with use of Trypan Blue #145-0021 manufactured by Bio-Rad Laboratories, Inc. A specific analysis method followed a protocol attached to each kit.

FIG. 7 shows test results. It was found that as illustrated in FIG. 7, in a sirolimus concentration-dependent manner, the cell proliferation was suppressed and the cell death was induced.

INDUSTRIAL APPLICABILITY

An embodiment of the present invention is applicable to a procedure or treatment for diffuse plexiform neurofibromas (e.g., diffuse plexiform neurofibromas developed on patients suffering from neurofibromatosis type 1).

The invention claimed is:

1. An external medicine for neurofibromas, comprising, (i) as an active ingredient, at least one selected from the group consisting of sirolimus, everolimus, temsirolimus, ridaforolimus, and zotarolimus and (ii) ethanol, the ethanol being contained in an amount of 20 wt % to 60 wt %, the active ingredient being contained in an amount of not less than 0.2 wt % and less than 0.8 wt %.

2. The external medicine as set forth in claim 1 is a gel.

3. The external medicine as set forth in claim 1, wherein the neurofibromas are diffuse plexiform neurofibromas.

4. A method of performing a medical procedure or medical treatment for neurofibromas, comprising the step of administering an external medicine comprising, (i) as an active ingredient, at least one selected from the group consisting of sirolimus, everolimus, temsirolimus, ridaforolimus, and zotarolimus and (ii) ethanol, the ethanol being contained in an amount of 20 wt % to 60 wt %, the active ingredient being contained in an amount of not less than 0.2 wt % and less than 0.8 wt %.

5. The method as set forth in claim 4, wherein the neurofibromas are diffuse plexiform neurofibromas.

* * * * *